US008117894B2

(12) United States Patent
Abdullah et al.

(10) Patent No.: US 8,117,894 B2
(45) Date of Patent: Feb. 21, 2012

(54) GAS SENSOR

(75) Inventors: Joel Abdullah, Austin, TX (US); Alexei Tikhonski, Cedar Park, TX (US); Ronald I. Dass, Austin, TX (US); James Novak, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 444 days.

(21) Appl. No.: 12/543,260

(22) Filed: Aug. 18, 2009

(65) Prior Publication Data
US 2010/0089122 A1 Apr. 15, 2010

Related U.S. Application Data

(60) Provisional application No. 61/090,444, filed on Aug. 20, 2008.

(51) Int. Cl.
*G01N 37/00* (2006.01)
(52) U.S. Cl. .............................. 73/23.2; 73/1.02; 340/634
(58) Field of Classification Search .................. 73/23.2, 73/1.02, 31.05
See application file for complete search history.

(56) References Cited

U.S. PATENT DOCUMENTS

| | | | | |
|---|---|---|---|---|
| 3,906,473 A | * | 9/1975 | Le Vine | 340/634 |
| 5,517,182 A | * | 5/1996 | Yasunaga | 340/634 |
| 5,886,638 A | * | 3/1999 | Tanguay | 340/632 |
| 5,898,101 A | * | 4/1999 | Lyle et al. | 73/23.2 |
| 7,820,949 B2 | * | 10/2010 | Sasaki et al. | 219/497 |
| 7,827,847 B2 | * | 11/2010 | Oishi et al. | 73/23.2 |
| 2009/0126454 A1 | * | 5/2009 | Pratt et al. | 73/1.02 |

OTHER PUBLICATIONS

Product Data Sheet "TGS 2442—for the detection of Carbon Monoxide," 2 pages.
Product Data Sheet "Technical Information for Carbon Monoxide Sensors," 13 pages.
Product Data Sheet "Signal Processing and Calibration Techniques for CO Detectors Using TGS 2442," 10 pages.
Madou, "Chemical Sensing with Solid State Devices," Academic Press, Inc. (1989), pp. 67-73.
Morrison, "The Chemical Physics of Surfaces," Second Edition, Plenum Press, (1977), pp. 251-259.
Ruhland, "Gas-kinetic Interactions of Nitrous Oxides with $SnO_2$ Surfaces," Sensors and Actuators B 50 (1998) pp. 85-94.

* cited by examiner

*Primary Examiner* — Hezron E Williams
*Assistant Examiner* — Hoang Nguyen
(74) *Attorney, Agent, or Firm* — Kelly Kordzik; Matheson Keys Garsson & Kordzik PLLC

(57) ABSTRACT

A sensor system issues measurement commands at a predetermined regular rate. If a measurement indicates that a gas of interest is present, then the sensor system is signaled to wake-up thereby pulsing a heater for the sensor element that improves the accuracy of measurements. Measurements of humidity, temperature and gas concentration are made. If the gas of interest is detected then the data is used to indicate a compensated gas measurement. The gas level is classified as to its hazard and an adaptive detection algorithm is used to set an activity mode. If the gas of interest is not detected, the adaptive detection algorithm is used to set a sleep mode that saves power. Measurement rates are kept constant while heater power is controlled to reduce power consumption. Measurement rates are changed to increase concentration sensitivity.

1 Claim, 10 Drawing Sheets

Fig. 1 - Model of inter-grain potential barrier (in the absence of gases)

GAS SENSOR

CROSS-REFERENCE TO RELATED APPLICATIONS

This application claims priority to U.S. Provisional Application Ser. No. 61/090,444, filed on Aug. 20, 2008, the entire contents of which are incorporated by reference herein.

TECHNICAL FIELD

The present invention pertains to heated metal oxide gas sensors, and in particular, to gas sensors based on tin oxide as a sensing material.

BACKGROUND

There is much information demonstrating the use of semiconducting metal oxides for gas sensors. The reaction mechanism begins with the absorption of ambient oxygen onto the metal oxide surface from the surrounding atmosphere. The adsorbed electro-negative oxygen molecules withdraw electron density from the surface of the metal oxide. This equilibrium shift in the electron density creates a depletion layer which lowers the baseline conductivity of the material relative to vacuum. Referring to FIG. 1, combined with surface structure, this depletion layer forms a potential barrier against electron flow. When the material is heated to several hundred degrees Celsius, the oxygen takes on a reactive form, $O^-_{ads}$. This adsorbed oxygen ion species can now react with the analyte gas so that a charge transfer reaction takes place. In one example, carbon monoxide reacts with the oxygen to form carbon dioxide. The generation of an electron on the semiconducting metal oxide surface by this reaction produces an increase in current. The amount of current is proportional to the concentration of CO that reacts with the adsorbed oxygen species on the metal oxide surface.

A typical metal oxide material for this reaction is tin (IV) oxide. To establish the conditions for the above reaction to occur, the surface temperature of $SnO_2$ is higher than 280° C. The amount of power required to heat this material to several hundred degrees is very large, usually exceeding several watts. This large power consumption greatly reduces the ability to power a sensor using a battery. While not impossible, the battery lifetime for operation is very short.

An example of this power requirement is the Taguchi gas sensor ("TGS") manufactured by Figaro Engineering Inc. ("Figaro"), which requires periodic heating to achieve high accuracy. The TGS currently pulses its heater once every second in its electronic set, with an average power consumption of 14 mW (milliwatts). This high power consumption is prohibitive to a battery-powered application.

SUMMARY

An embodiment of the sensor system of the present invention incorporates a gas sensor, such as a TGS, which includes setting the gas sensor to a sleep mode for a time period followed by a start-up mode. The gas sensor is sampled at regular time intervals to ascertain the presence of a desired gas, wherein the gas sensor is operated at a reduced accuracy in the sleep mode. The gas sensor is awoken after the period of time, and a heater affecting the accuracy of the gas sensor is pulsed. The gas sensor is then returned to a sleep mode for a second time period, which determines when the data is ready to be acquired following the pulsing of the heater. Measurements may be taken to determine a concentration of the desired gas and levels of parameters used to compensate the gas measurement. The indicated compensated level of gas concentration may be used to classify the desired gas as to its hazard level. An adaptive detection algorithm may be used to set a sleep mode if the desired gas is not detected and to set an activity mode in response to the hazard level if the gas is detected. The heater pulse rate may be adaptively varied in response to a level of the desired gas concentration and assessed hazard level to control a power level required to operate the sensor system.

DETAILED DESCRIPTION

Figure 1:
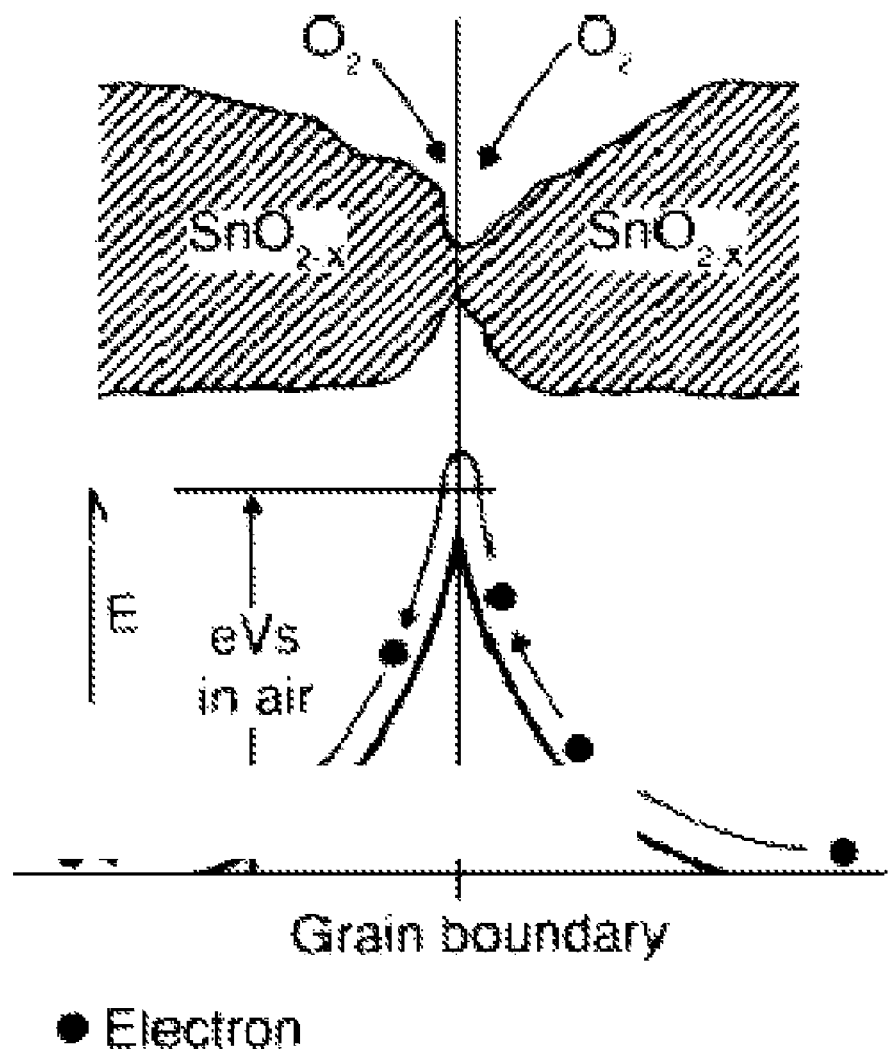
FIG. 1 illustrates a model of an inter-grain potential barrier.

A combination of hardware and/or software techniques allows for a sensor system with full system power limited to less than 2.2 mW. Embodiments have a combination of high performance and extremely low power technology. In embodiments, a microcontroller is utilized with several different advanced sleep modes, which allows for power conservation during non-active periods. Other electronic components are extremely low power as well. This adaptive pulsed heating method may be implemented to change the sensor sensitivity.

The importance of this heating method may be emphasized by considering the detailed chemistry which occurs on the surface of the metal oxide semiconductor. All metal oxide sensors react through the same three step mechanism. M. J. Madou and S. R. Morrison, *Chemical Sensing with Solid State Devices*, (Academic Press, 1989), p. 67; S. R. Morrison, *The Chemical Physics of Surfaces*, 2$^{nd}$ edition, (Plenum Press, 1990), p. 251; and B. Ruhland, Th. Becker, and G. Müller, Sens. Actuat. B 50, 85 (1998). First, diatomic oxygen from the ambient environment is chemisorbed onto the oxide-ion-deficient surface as the negatively charged dioxygenyl anion species $O^-_2$ or the more reactive $O^-$ The oxygen captures an electron from the metal center of the metal oxide crystal structure. This leaves a negatively charged oxygen species on the surface and a positively charged metal center (e.g., tin). This charged oxygen is then free to react with analyte molecules. In the case of carbon monoxide, the reaction proceeds according to the following oxidation reaction:

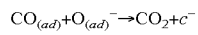

$$CO_{(ad)} + O_{(ad)}^- \rightarrow CO_2 + e^-$$

This reaction is considered a second step in the mechanism. Carbon monoxide reacts with the surface bound oxygen to create carbon dioxide while leaving an electron behind in the crystal structure of the metal oxide. The result of this reaction is a change in conductivity that can be explained by two possible mechanisms: the reduction in grain boundary-induced barrier heights due to the removal of the adsorbed oxygen species, or the increase in carrier concentration as a result of the mobile electron. This change in conductivity can be measured as a change in resistance or a change in current. Since one electron is produced for each molecule of carbon monoxide reacted, a simple calibration curve can be generated which correlates the number of molecules of CO (concentration) and the change in sensor conductivity (response).

Embodiments of the present invention have an impact on the first step in the reaction mechanism. The reactive species (as described above) is the surface adsorbed O—. It is well known in surface chemistry that the chemisorbed ionic species can have very long lifetimes after much energy is introduced to create them. In heated metal oxide sensors, the O— is created with thermal energy. What many studies do not investigate is the surface kinetics of these chemisorbed species. Embodiments of the present invention not only demonstrate the generation of the adsorbed oxygen species, but also determine how their surface reactivity changes with temperature and time. The cooler surface temperature increases the low concentration sensitivity due to the lack of thermal diffusion currents, which control analyte delivery. Further, a cooler surface temperature enhances the lifetime of the chemisorbed oxygen species, which therefore provides favorable conditions for their facile reaction with a low concentration of CO or other analyte molecules.

The adaptive heater pulse demonstrates that the lifetime of the reactive oxygen species on the surface is very long compared to the pulse duration of the heater. This means that a stable species can be generated with a short heated pulse to create an, albeit brief, high temperature state where the reactive oxygen atoms would remain on the surface even after the sensor has cooled down. Once the sensor has cooled, an increase in sensitivity at these lower temperatures is observed.

Figure 6:
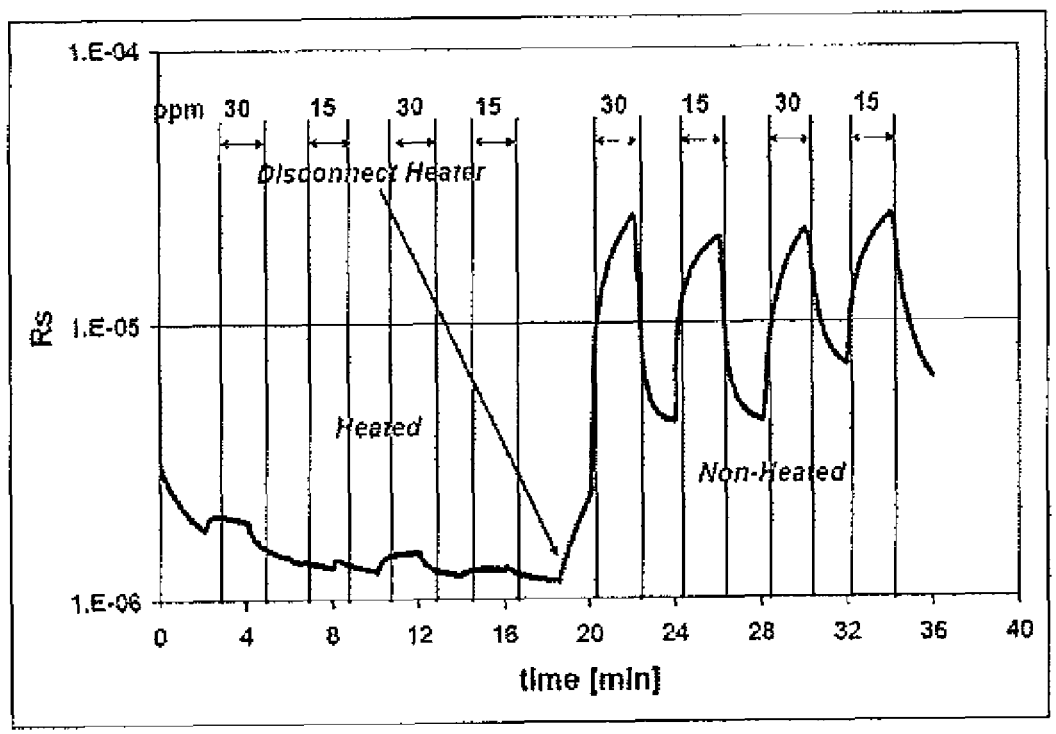
FIG. 6 illustrates a Figaro TGS 2442 sensor response shown with and without the manufacturer's recommended heating cycle.

To demonstrate, a voltage was applied to the heater trace. A series of 30 and 15 ppm (parts per million) deliveries of CO were made to the sensor at 2 minute intervals. In the first series, the heater was driven according to the manufacturer's recommended 1.5% duty cycle with a time interval of 1 second (sec). FIG. 6 shows that when the heater is turned on, the 30 ppm exposure is barely visible, and the 15 ppm deliveries are indistinguishable from the baseline. In contrast, when the heater is turned off after it was initially on for a period of time, the surface oxygen species are now stabilized so that a reaction with the CO molecules can easily occur and the sensor now responds. The second half of the trace shows the large response of the sensor to 30 and 15 ppm in this mode of operation. These results support the manufacturer data that TGS sensors are not sensitive below 30 ppm, but implementation of embodiments of the present invention enables high sensitivity to low concentrations. Rs is defined as the uncorrected sensor response.

These results clearly support a non-heated sensor having a greater sensitivity. A next step includes the determination of the time interval which is required to increase the temperature above 250° C. At this temperature, which is maintained for a short period of time, creation of the reactive chemisorbed oxygen species occurs that will maximize the sensor's sensitivity when it is operated in the non-heated mode described earlier.

Figure 2:
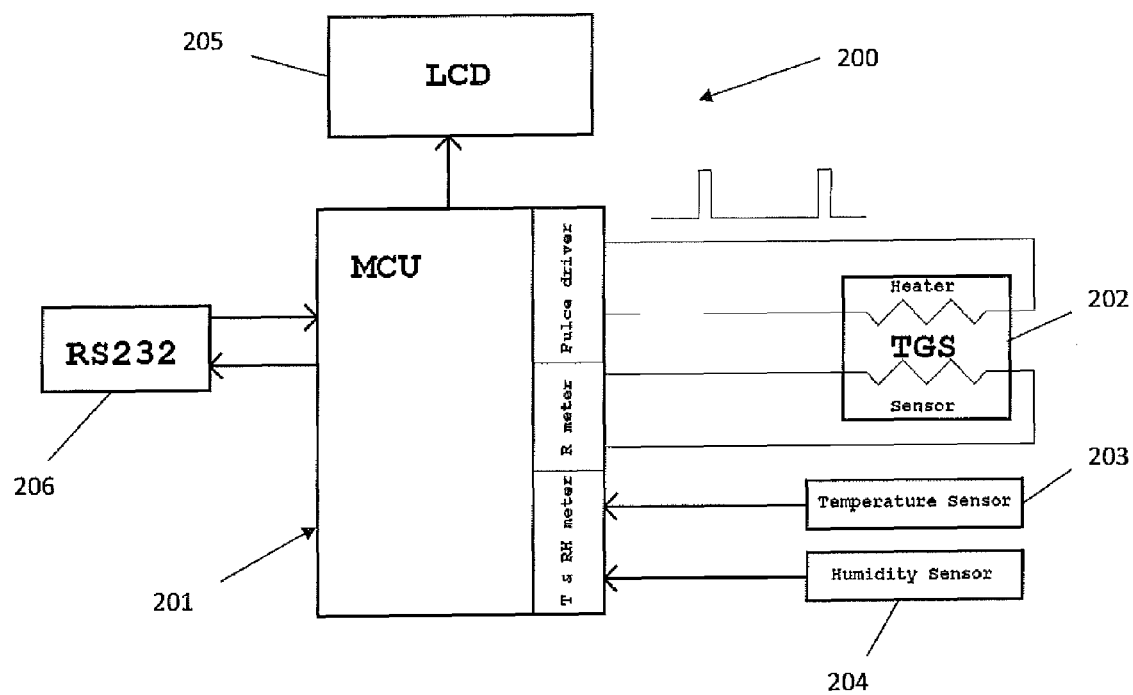
FIG. 2 illustrates an embodiment of the present invention.
Figure 7:
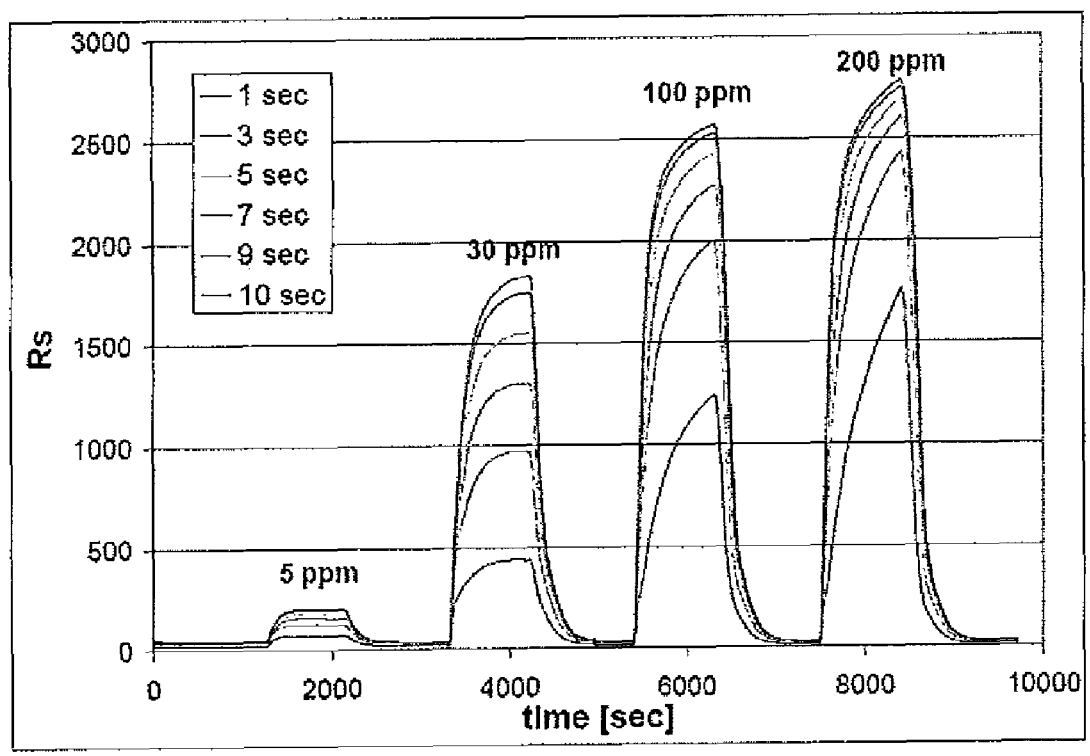
FIG. 7 illustrates a room temperature response of a TGS modified in accordance with embodiments of the present invention.

Referring to FIG. 2, embodiments of the sensor system 200 comprise a TGS 202 modified with electronics 201 that allow control over the sensor heating cycle. Electronics 201 may be implemented with a software algorithm and some hardware based upon a microcontroller unit (MCU) used to execute the algorithms as discussed herein. The MCU controls the functions of the heater, output display (LCD) 205, external connections (RS232) 206, and TGS 202. The MCU has a resistance meter to measure the change in the TGS 202 sensor element. The MCU controls the pulse driver that delivers the heater pulse algorithms to the heater circuit in the TGS 202. The MCU may also receives signal inputs from external temperature 203 and humidity 204 sensors. This input may be used to correct for drift of the TGS 202 due to environmental changes. In embodiments, the heater is pulsed for 15 ms, and then a period of time passes before again applying the next pulse. FIG. 7 shows a graph of a room temperature response of a TGS modified to be accompanied with a system configured in accordance with an embodiment of the present invention. The graph shows a standard CO delivery test containing 5, 30, 100, and 200 ppm CO with a recovery of clean air between each concentration, which allows a measurement of the sensor response time to the CO gas and the recovery time. The same delivery is graphed as a function of heater pulse rate in Seconds. It can be seen in the graph that the sensor system has a much greater response at low concentrations the longer the wait between heating pulses. This has two positive effects on the sensor. First, by waiting 10 seconds between pulses, the sensor apparatus is using an order of magnitude less power. Second, the increased time between heater pulses provides the sensor system with an increased sensitivity by nearly a factor of 5. From the upslope of the sensor response for each concentration, the sensor system has a faster response time without a sacrifice in the recovery time.

Figure 8:
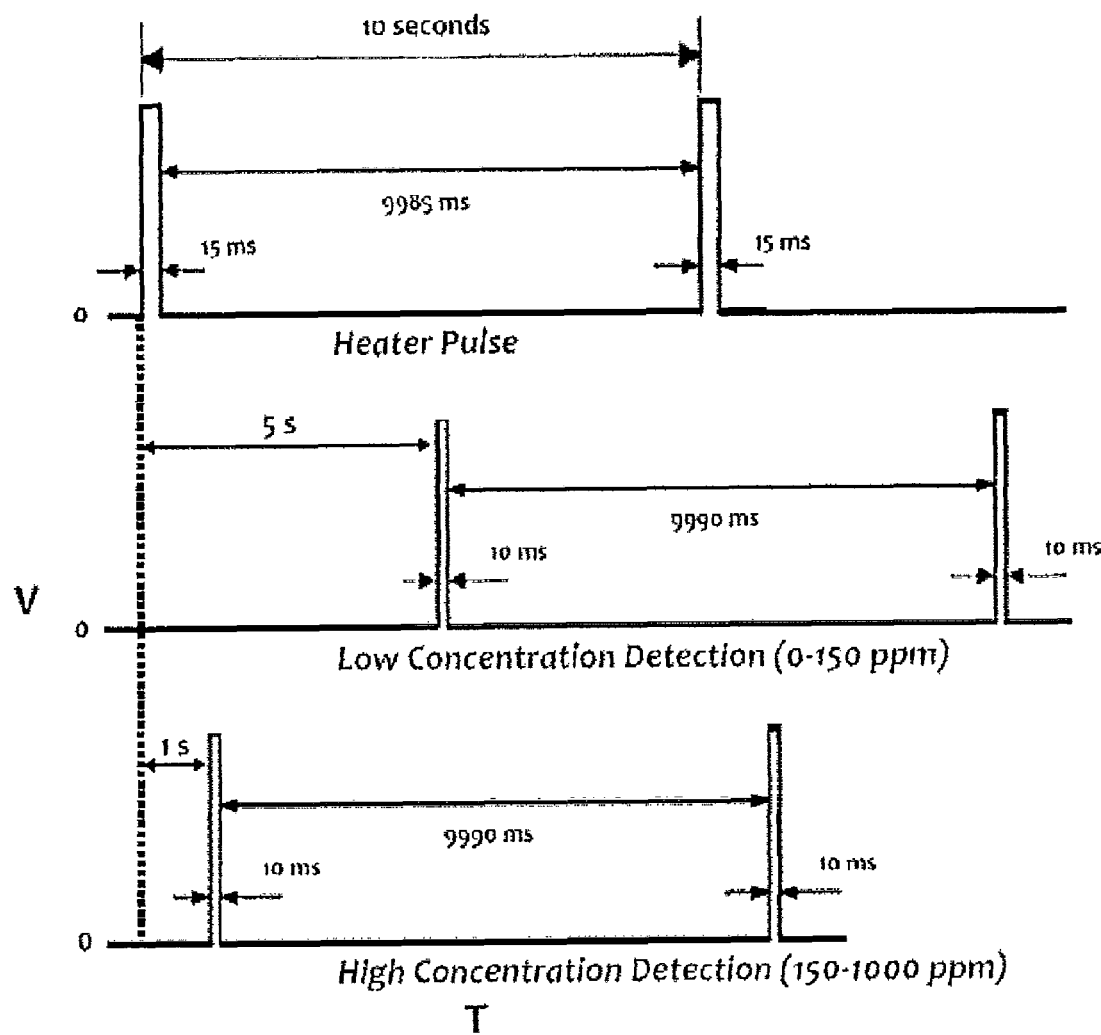
FIG. 8 illustrates a concentration dependent variable heat pulse cycle and detection point.

In embodiments, a pulsed heating cycle is utilized for CO sensing where a 15 ms heat pulse occurs once every 10 seconds. The sensing element surface temperature reaches more than 300° C. during heating, while the detection point occurs at room temperature. During this 10 second time interval, there are two detection events that are concentration dependent. Initially, the sensor measurement cycle occurs every 10 seconds, 5 seconds into the heating cycle. When the concentration exceeds 150 ppm CO, the measurement occurs at 1 second past the heater pulse. These time intervals provide the best combination of sensitivity, power consumption, stability and accuracy. The 10 ms detection point occurs at 5 seconds into the 10 second heating cycle as illustrated in the graph in FIG. 8. Each 10 second $V_H$ cycle includes a 4.5 V (volt) pulse for 15 ms followed by 0 V for 9985 ms. Each 10 second $V_c$ cycle is comprised of 10 ms at 3.3 V followed by 9990 ms at 0 V.

Power conservation is achieved via adaptive pulsed heating. The sensor system according to embodiments could be analogous to a periodic heart beat. After each beat, the sensor system calculates the carbon monoxide (CO) concentration using data from the three sensors: a CO sensor, a temperature sensor, and a humidity sensor. If CO is not present for a defined number of measurements, the firmware reduces the frequency of heater operation. It is important to understand that the sensor system does not reduce the measurement cycle, but the heating cycle. After many measurements during which no CO is detected, the sensor system reduces the heating cycle to a deep sleep over a time period. When measurements indicate that CO is present, the sensor system pulses the heater, assesses the "threat" level of the gas concentration, and based on several factors may go into one of the defined active modes: (1) becoming active (pulsing heater often), (2) extremely active (maximum sensitivity and power consumption), or (3) returning to one of several possible sleep states. Exemplary timing diagrams are shown in FIGS. 3A-3C.

Figure 3A:
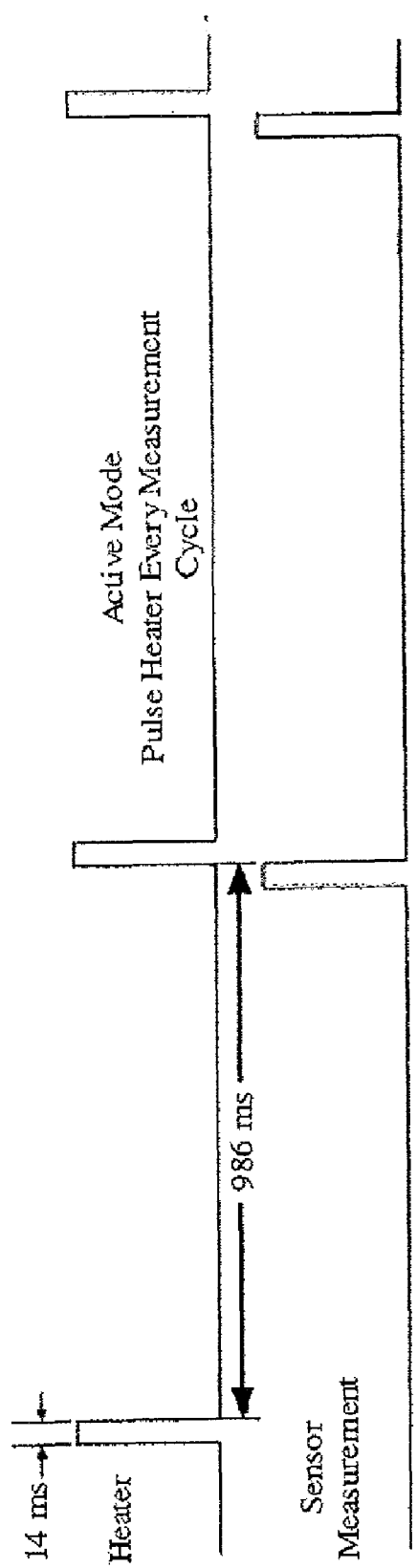
FIG. 3A illustrates pulses in an operation mode.

In FIG. 3A, the sensor system is in an active mode wherein the heater is pulsed at a same rate at which the measurements are taken. This occurs in the case when there is a perceived CO threat. In the active mode, the sensor measurement cycle may be once per second. In this embodiment, the heater may be pulsed for 14 ms and also once per second, synchronous with the sensor measurement cycle.

Figure 3B:
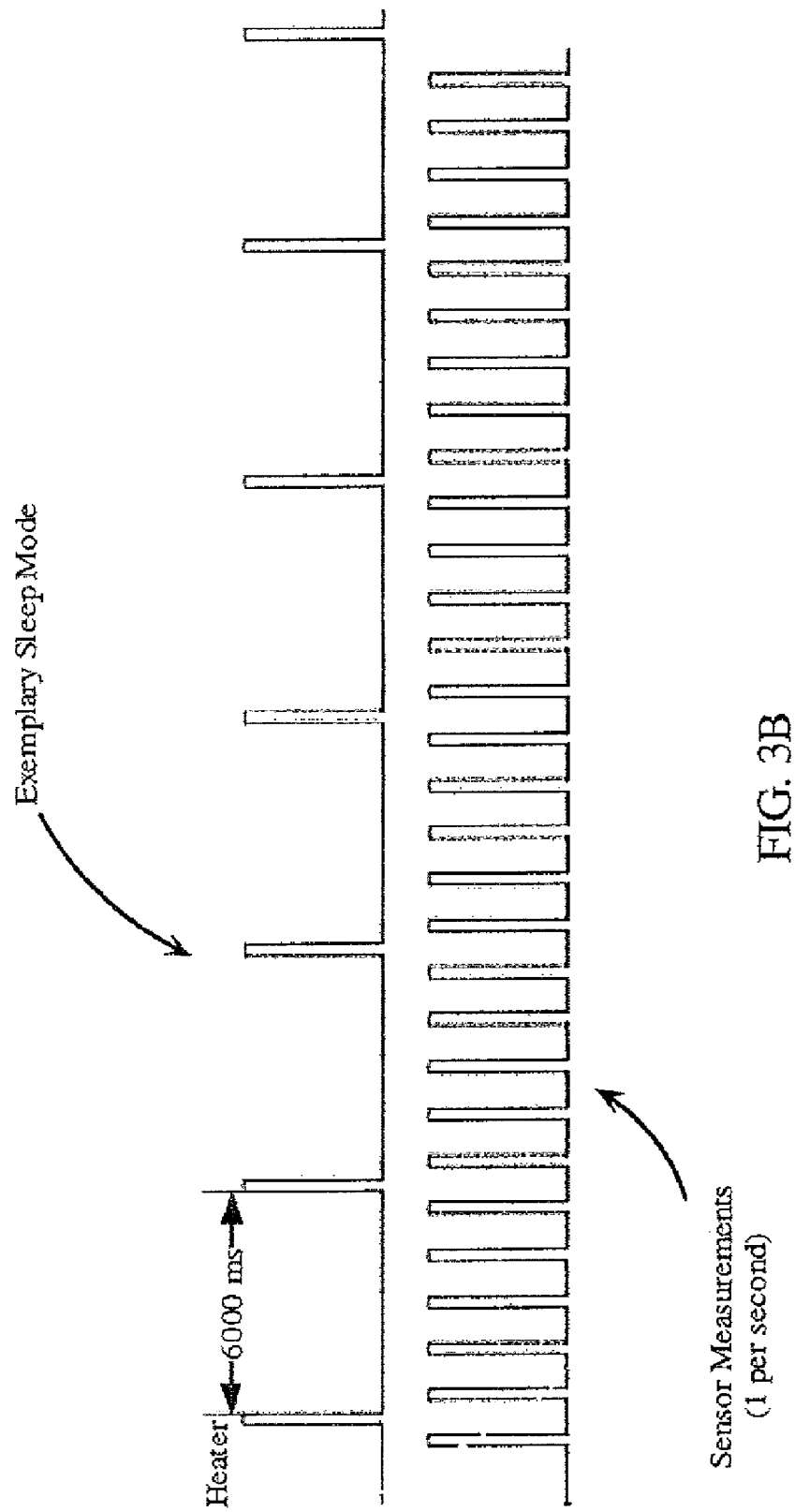
FIG. 3B illustrates pulses in another operation mode.
Figure 3C:
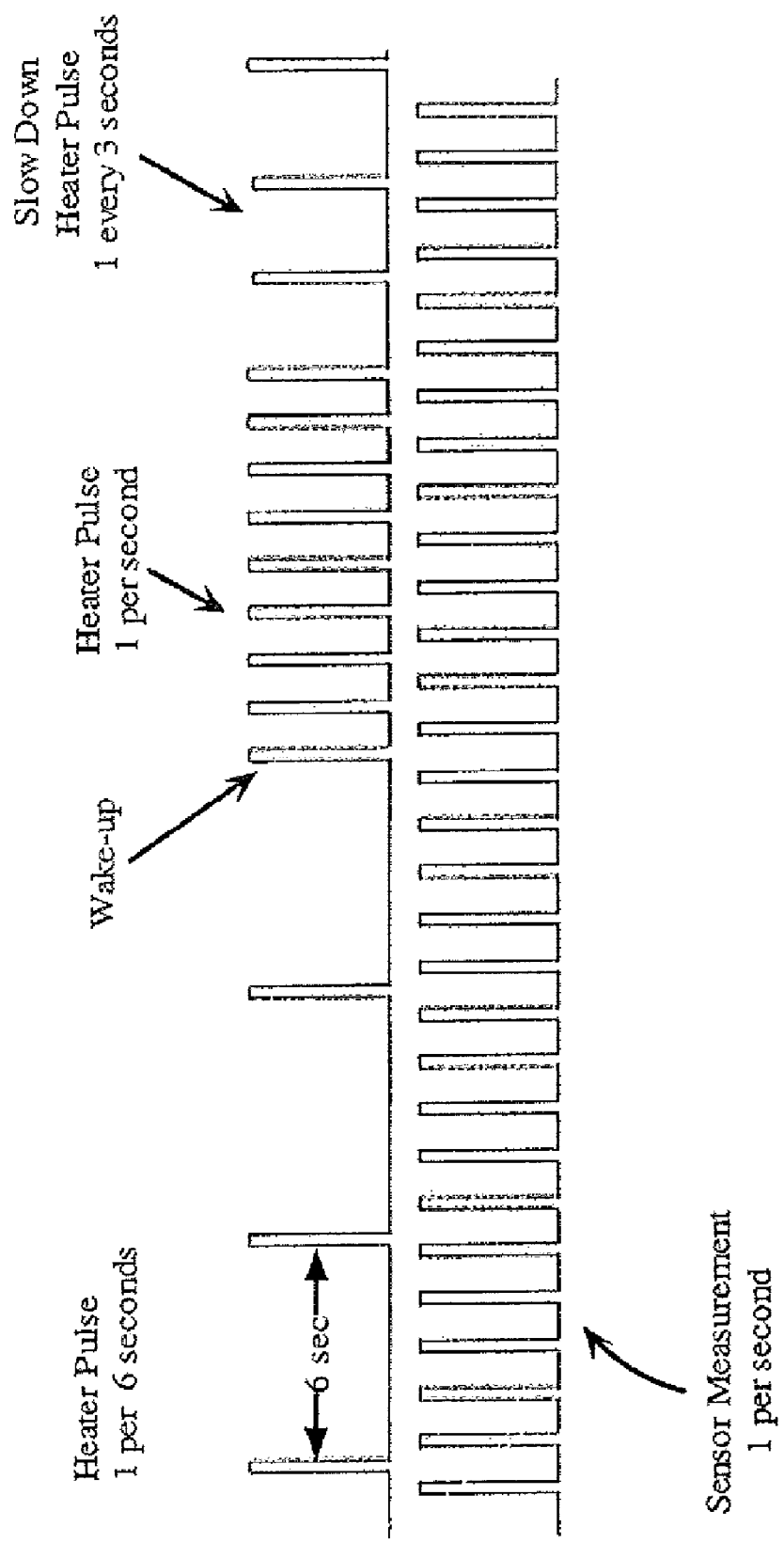
FIG. 3C illustrates pulses in another operation mode.

FIG. 3B illustrates a lower activity sleep mode wherein measurements may occur once per second while the heater may be pulsed once every six seconds. FIG. 3C illustrates a case where the sensor system is initially in a sleep state, where the heater may be pulsed every six seconds and measurements may be taken once per second. After a time period, CO detection occurs and the sensor system wakes up. During wake-up, the heater may be pulsed once per second corresponding to the measurement cycle. The firmware first decides if the CO level detected represents a high enough threat to switch to a fully active mode. However, in this particular case, the adaptive firmware makes a decision that the CO concentration is reduced to the point that warrants a less aggressive detection mode. In this slow down, the heater pulse rate is again decreased.

In embodiments of the sensor system, the initial system start up may first execute a cleaning cycle to remove all chemical contaminants from the sensor. The sensor system then switches to a sleep mode until the first measurement period. In one exemplary case where the default measurement period is 10 seconds, the sensor system creates a single heater pulse for 15 ms after 9 seconds, wherein the measurements are configured to occur every 10 seconds. In FIGS. 3A-3C, timing is synchronized via a pulse that occurs every second and is referred to as the system "heartbeat." The sensor system returns to a sleep mode during periods between heating cycles and measurement cycles. Since the accuracy of the sensor system gas measurement is a function of the frequency of the heater pulse, the sensor system increases the rate at which the heater operates to improve the accuracy of the measurement thereby sacrificing the battery life of the sensor system. However, since the majority of the operation time is conducted in an environment where a gas of interest is not present, the sensor system actually reduces the heater cycles and conserves battery life. In embodiments described herein, data measurements are taken at the same rate. Reducing the rate of heater cycles, therefore, does not increase the chance of not detecting a gas of interest.

The following logic flow illustrates a sensor system operation:
1) Start-up—System will load calibration data, run a clean sensor routine, and run a self-test, wherein reference measurements may also be taken.
2) Sleep—Following Start-up, the sensor system proceeds into a sleep mode. The initial wake period of the sensor system may be variable based on preconfigured parameters set by the user. For example, a particular default sleep setting may be 10 seconds, which is used in the present example.
3) Wake-up—The heartbeat signal may occur once per second and used to coordinate activity in the sensor system. Once the first wake-up cycle is triggered, the sensor system pulses the heater and then returns to a sleep mode for an additional 985 ms waiting until data is ready to be read. After the 985 ms, the gas concentration, humidity, and temperature measurements may be taken.
4) After a gas measurement (e.g., CO), data is loaded into an algorithm that guides the operation of the sensor system.

If the desired gas (e.g., CO) is not detected:
5) Data is loaded to the algorithm for use with future measurements.
6) One of several possible sleep modes is entered. In an example where CO is not detected in the last recent measurements, the sensor system may return to a deep sleep mode. (10 second heater interval in the case of the stated example).

If the desired gas (e.g., CO) is detected:
7) The CO measurement is first compensated for temperature and humidity, and then it is determined whether the concentration poses an immediate threat requiring audio or visual alarm.
8) Data is fed to the adaptive algorithm, which then refers to the programmed alarm thresholds stored in the device's memory.

The proximity of the actual CO concentration to a defined dangerous level is one example of a user setting that allows the behavior of the sensor system to be changed based on the application specific requirements. In the case where the CO concentration is far below the threshold warning, the likelihood that the sensor system switches into a deep sleep mode would be greater than in the case where the CO gas concentration is only slightly below a warning threshold. For this reason, a stored array of threshold values is maintained that provides the sensor system a methodology for assessing a threat and allows adaptive behavior based on desired gas (e.g., CO) concentration.

Figure 4:
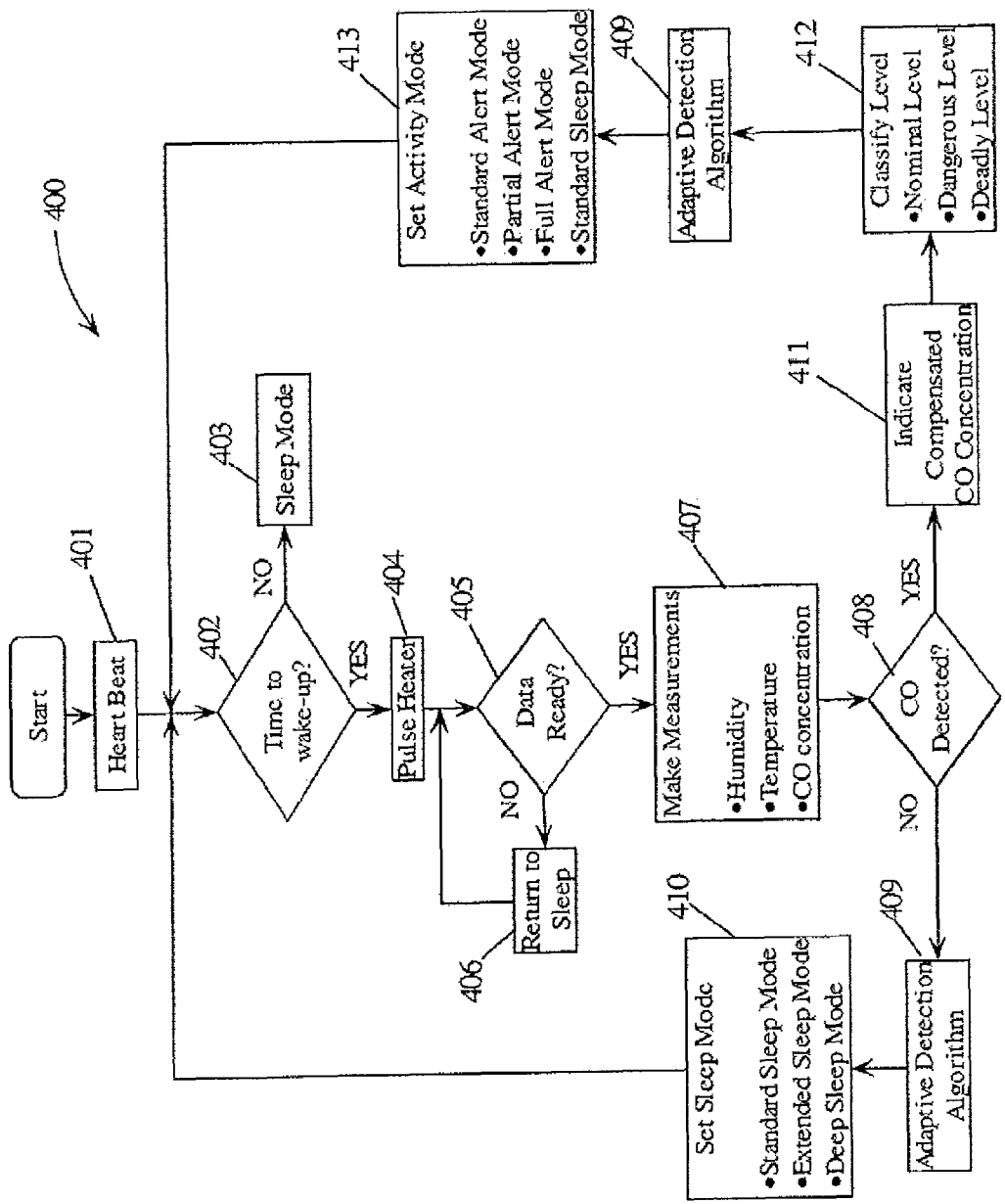
FIG. 4 illustrates a flow diagram in accordance with an embodiment of the present invention.

FIG. 4 is a flow diagram 400 of method steps used in embodiments herein. The sensor system starts in response to heart beat signal 401 that occurs at a regular rate (e.g., once per second). In step 402, a determination is made whether it is time for the sensor system to wake up. This occurs when a sensor measurement indicates a gas of interest is present. If step 402 does not indicate wake-up, then in step 403 a sleep mode is re-entered. If step 402 indicates a wake up is necessary, then in step 404 the heater is pulsed with a predetermined pulse width. In step 405, a determination is made whether measurement data is ready. If data is not present, then in step 406 a return to a sleep mode is made. If data is ready, then in step 407 measurements of temperature, humidity, and desired gas (e.g., CO) concentration are made. In step 408, a test is performed to determine if the desired gas (e.g., CO) is detected. If no desired gas is detected, then in step 409 an adaptive detection algorithm is executed that determines which sleep mode in step 410 to enter. A return is executed to step 402 awaiting "wake-up."

If the desired gas is detected in step 408, then in step 411 the compensated concentration of the desired gas (CO) is indicated. In step 412, the hazard level of the desired gas is classified as nominal, dangerous, or deadly. In step 409, the adaptive algorithm is again executed to determine what activity mode to set. In step 413, either the standard, partial, or full alert mode is selected, or the standard sleep mode entered.

Figure 5:
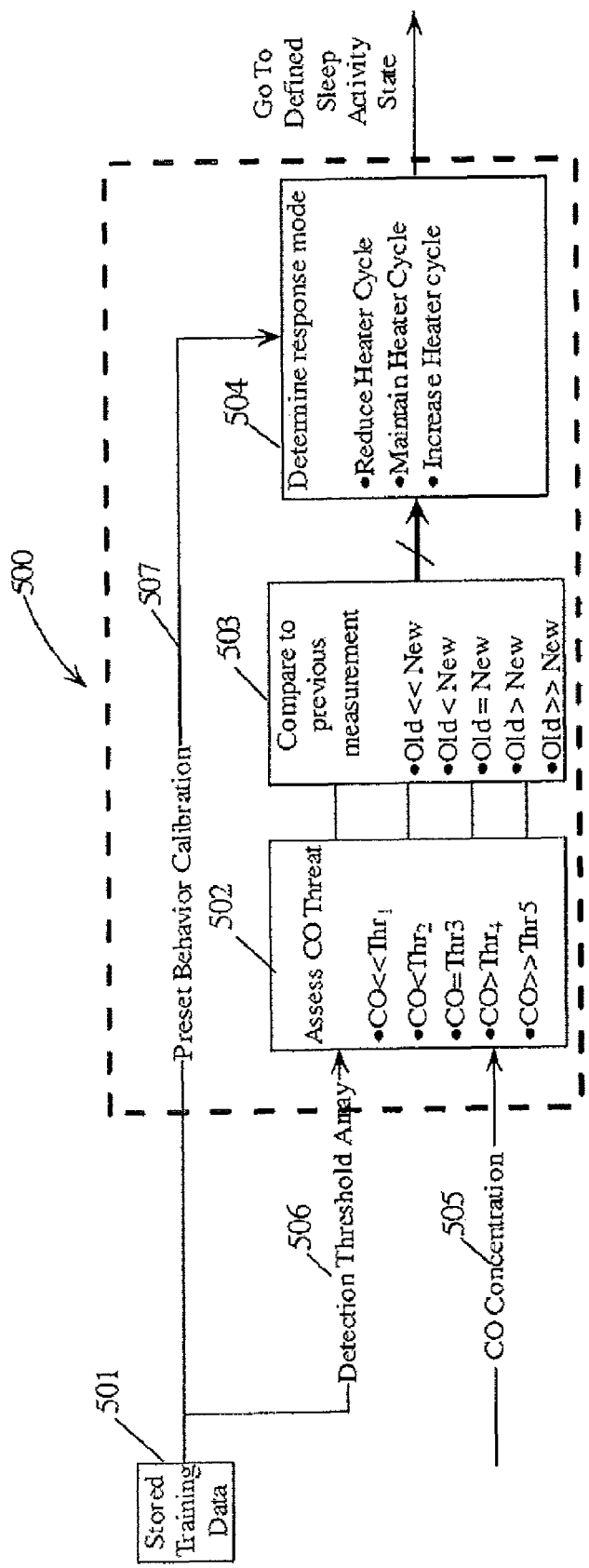
FIG. 5 illustrates a block diagram of an algorithm used in embodiments of the present invention.

FIG. 5 illustrates a block diagram of features of the adaptive algorithm. Stored training data 501 is used for preset behavior calibration 507 and to provide a detection threshold array 506. The CO concentration 505 comes from step 411 in FIG. 4. The CO threat 502 is assessed by comparing the CO concentration 505 against a number of threshold values. In 502, the CO concentration 505 is compared against five threshold values Thr1-Thr5 and classified as (CO<<Thr1), (CO<Thr2), (CO=Thr3), (CO>Thr4), and (CO>>Thr5). In 503, a comparison is made between the old measurement (Old) and new measurements (New). The exemplary comparison in 503 classifies the comparison as: (Old<<New), (Old<New), (Old=New), (Old>New), and (Old>>New). The assessment 502 and comparison 503 are used to determine a response mode, for example: (reduce heater cycle), (maintain heater cycle), (increase heater cycle), or go to a defined sleep activity state.

While the embodiments described herein are described with certain specific characteristics, they are not intended to limit the scope of the invention to the particular forms set forth, but, on the contrary, it is intended to cover such alternatives, modifications, and equivalents as may be included within the spirit and scope of the invention as defined by the appended claims. Embodiments of the present invention are described herein with respect to a modified TGS 2442, but such embodiments are not limited as such, but may be implemented with other gas sensors without diverting from aspects of the present invention.

What is claimed is:

1. A method of operating a sensor system comprising:
setting the sensor system to a sleep mode for a first time period;
sampling a gas sensor at time intervals to ascertain a presence of a gas, wherein the gas sensor is operated at a reduced accuracy in the sleep mode;
waking up the sensor system after the first time period;
pulsing a heater to affect an accuracy of the gas sensor;
returning to a sleep mode for a second time period;
taking a measurement for determining a concentration of the gas and parameters for compensating the measurement of the concentration of the gas after the second time period;
indicating a compensated level of gas concentration if the gas is detected;
classify the gas as to its hazard level;
using an adaptive detection algorithm to set a sleep mode if the gas is not detected and to set an activity mode in response to the hazard level if the gas is detected; and
varying the heater pulse rate in response to the level of the gas concentration and the hazard level.

* * * * *